United States Patent [19]

Shore et al.

[11] 4,349,521

[45] Sep. 14, 1982

[54] RUTHENIUM CARBONYLATES, RUTHENIUM CARBONYL HYDRIDES, OSMIUM CARBONYLATES AND THEIR PREPARATION

[75] Inventors: Sheldon G. Shore, Columbus, Ohio; Colleen C. Nagel, St. Paul, Minn.

[73] Assignee: The Ohio State University Research Foundation, Ohio

[21] Appl. No.: 274,152

[22] Filed: Jun. 16, 1981

Related U.S. Application Data

[63] Continuation-in-part of Ser. No. 127,214, Mar. 4, 1980, abandoned.

[51] Int. Cl.$^3$ .................... C01G 1/04; C01G 55/00; C07F 15/00
[52] U.S. Cl. .................................. 423/417; 423/418; 260/429 R
[58] Field of Search .............................. 260/429 R; 423/416–418

[56] References Cited

U.S. PATENT DOCUMENTS

| 3,514,258 | 5/1970 | Bruce et al. | 423/417 |
| 3,786,132 | 1/1974 | Dawes et al. | 423/417 |
| 4,217,249 | 8/1980 | McVicker | 252/466 |

OTHER PUBLICATIONS

Vaglio et al., "Isomerization of Pentenes Catalyzed by Ruthenium Cluster Carbonyls Tranition Met", Chem. vol. 2, pp. 94–97 (1977).
Canty et al., "Organoruthenium clusters obtained from $\alpha$-H$_4$ Ru$_4$ (CO)$_{12}$", J. Organometallic Chemistry, vol. 43, pp. C-35–C38 (1972).
Eady et al., "[HRu$_6$(CO) 18]: a Ruthenium Anion Having an Interstital H-Ligand. X-Ray Crystal Structures of Two Modifications", J.C.S. Chem. Comm., pp. 945–946 (1976).
Ford et al., "Homogeneous Catalysts of the Water Gas Shift Reaction by Mixed–Metal (Iron/Ruthenium) Catalysts". J.A.C.S., vol. 100, pp. 4797–4799 (1978).
Ungermann et al., "Homogeneous Catalysis of the Water Gas Shift Reaction by Ruthenium and Other Metal Carbonyls. Studies in Alkaline Solutions". J.A.C.S. vol. 101, pp. 5922–5929, 1979.
Johnston et al., "Chemistry of Polynuclear Compounds. Part XII, Polynuclear Hydriodo–Carbonyls of Ruthenium", J. Chem. Soc. (A), pp. 2856–2859 (1968).
Knight et al., "A Study of the Reaction of the Series of Neutral Metal Carbonyls M$_3$ (CO$_{12}$) (M–Fe, Ru, or Os) with the Metal Carbonyl Anions [M$^1$ (CO)$_5$] (M–Mn or Re)", J.C.S. Dalton, pp. 1022–1029 (1971).
Eady et al., "The Chemistry of Polynuclear Compounds. Part XXVI. Products of the Pyrolysis of Dodecacarbonyl-triangulo-triruthenium and triosmium", J.C.S. Dalton, pp. 2606–2611, 1975.
Eady et al., "The Chemistry of Polynuclear Compounds. Part 29. Products of the Reaction of Triruthenium and Triosmium Dodecacarbonyls with Water", J.C.S. Dalton, pp. 838–844 (1976).

*Primary Examiner*—Earl C. Thomas
*Attorney, Agent, or Firm*—Millard & Cox

[57] ABSTRACT

Disclosed are the novel cluster compounds [HRu$_4$(CO)$_{13}$]$^{1-}$, [Ru$_4$(CO)$_{13}$]$^{2-}$, [Ru$_4$(CO)$_{12}$]$^{4-}$, [HRu$_4$(CO)$_{12}$]$^{3-}$, and salts thereof, and H$_4$Ru$_4$(CO)$_{12}$. Also disclosed are novel procedures for synthesizing these cluster compounds in high yield. Further disclosed is a novel procedure for making H$_2$Ru$_4$(CO)$_{13}$ and H$_4$Ru$_4$(CO)$_{12}$ in high yield. Also disclosed are [Ru$_3$(CO)$_{11}$]$^{2-}$ and the corresponding osmium dianion.

118 Claims, No Drawings

RUTHENIUM CARBONYLATES, RUTHENIUM CARBONYL HYDRIDES, OSMIUM CARBONYLATES AND THEIR PREPARATION

The government has rights in this invention pursuant to grant CHE-76-18705 awarded by the National Science Foundation.

This application is a continuation-in-part of our copending application Ser. No. 127,214 filed Mar. 4, 1980, and now abandoned.

BACKGROUND OF THE INVENTION

The present invention relates to new high yield syntheses of ruthenium carbonylates, to new tetraruthenium hydridocarbonylate anionic species and to synthesis of osmium carbonylates.

The tetranuclear cluster $H_2Fe_4(CO)_{13}$ and its conjugate bases, $[HFe_4(CO)_{13}]^{1-}$ and $[Fe_4(CO)_{13}]^{2-}$, have been known for over twenty years. While the ruthenium analog, $H_2Ru_4(CO)_{13}$, also is well known, its conjugate bases, $[HRu_4(CO)_{13}]^{1-}$ and $[Ru_4(CO)_{13}]^{2-}$, have eluded isolation and identification, even though their possible presence in solution has been theorized by Ford et al, *JACS*, 100, 4797–4799 (1978); Ungermann et al, *JACS*, 101, 5922–5929 (1979); and Johnson et al, *J. Chem. Soc.* (A), 2856–2859 (1968). Even though the tetraruthenium anion has eluded isolation and identification, such anion and $H_2Ru_4(CO)_{13}$ have been implicated as active species in catalytic systems by Ford et al, supra, by Ungermann et al, supra, and by Vaglio et al, *Trans. Met. Chem.*, 2, 94 (1977).

The neutral compound, $H_2Ru_4(CO)_{13}$, heretofore, has been obtained only as a side product in low yields in a variety of reactions. Johnson et al, supra; Canty et al, *J. Organometal Chem.*, 43, C35–C38 (1972); Eady et al, *J.C.S. Chem. Comm.*, 945–946 (1976); Knight et al, *J.C.S. Dalton*, 1022–1029 (1971); and Eady et al, *J.C.S. Dalton*, 2606–2611 (1975). Further, Johnson et al, supra, have reported reduction reactions of $Ru_3(CO)_{12}$, however, such reduction reactions were found to be nonspecific and yielded highly complex mixtures.

The present invention provides a new controlled reduction reaction for the synthesis, isolation and characterization of the above-mentioned dianion and also a new highly charged tetraanion. Synthesis of the anion $[HRu_4(CO)_{13}]^{1-}$ also is reported. The invention also provides methods for the protonation of the aforementioned tetraanion to produce the species $[H Ru_4(CO)_{12}]^{3-}$, $[H_2Ru_4(CO)_{12}]^{2-}$, $[H_3 Ru_4(CO)_{12}]^{1-}$ and $H_4Ru_4(CO)_{12}$, the first of which is itself novel. Finally, the invention provides a method for the synthesis of the anions $[Os_3(CO)_{11}]^{2-}$ and $[Ru_3(CO)_{11}]^{2-}$.

STATEMENT OF THE INVENTION

One aspect of the present invention is a method for making $[Ru_4(CO)_{13}]^{2-}$ by a carefully controlled reduction of $Ru_3(CO)_{12}$. This method comprises establishing a reaction mixture held under substantially anhydrous and oxygen-depleted conditions at a temperature not above about room temperature (about 25° C. for present purposes) of the $Ru_3(CO)_{12}$, an alkali metal, a carrier compound which will carry solvated electrons from said alkali metal, and a solvent which will solubilize electrons from said alkali metal. The molar ratio of the alkali metal to the $Ru_3(CO)_{12}$ reactant is restricted to be at least about 1.5:1 but less than 3:1. A salt of the dianion may be recovered from the reaction mixture if desired.

Another aspect of the present invention is a method for making $[HRu_4(CO)_{13}]^{1-}$. This method comprises establishing a reaction mixture comprising a solvent containing the anion $[Ru_4(CO)_{13}]^{2-}$ dissolved therein and a protic acid, including water for this reaction. The molar ratio of said protic acid to said dianion ranges from between about 1:1 to about 2:1. The reaction mixture is established under conditions substantially free of molecular oxygen at a temperature not substantially above about room temperature. The novel $[HRu_4(CO)_{13}]^{1-}$ may be recovered in salt form from the reaction mixture if desired. The reduction and protonation reactions may be conducted in the same or separate steps i.e. the reaction mixture from the reduction of $Ru_3(CO)_{12}$ may have the protic acid added thereto, or a salt of the $[Ru_4(CO)_{13}]^{2-}$ anion may be separated and protonated in a separate step.

A further aspect of the present invention is a method for making $H_2Ru_4(CO)_{13}$ in high yields. This method comprises adding a protic acid to a reaction mixture containing the dianion or anion disclosed above. The protic acid is added in a substantial stoichiometric excess relative to the dianion or anion in the reaction mixture. The temperature of the reaction mixture is maintained at about room temperature or less during this protic acid addition. Yields of about 75% or more based on the $Ru_3(CO)_{12}$ feed used to make the anion or dianion can be realized by this synthesis. Again, this reaction may be effected either with or without isolation of $[Ru_4(CO)_{13}]^{2-}$ and $[H Ru_4(CO)_{13}]^{1-}$ salts.

A still further aspect of the present invention is a method for making $[Ru_4(CO)_{12}]^{4-}$. One embodiment of this method comprises establishing the reaction mixture required to make the dianion as disclosed above with the following exceptions. The reaction mixture is established at a temperature not above about 80° C., and preferably not above about 50° C., and the molar ratio of the alkali metal to the $Ru_3(CO)_{12}$ feed is at least about 1.5:1, and preferably at least about 3:1. At molar ratios between 1.5:1 and 3:1, a mixture of products is formed, maximum yields being achieved with molar ratios of 3:1 or more. Another embodiment of this method comprises establishing a reaction mixture substantially identical to the reaction mixture established for the first embodiment, except that the triruthenium carbonylate feed is $[Ru_4(CO)_{13}]^{2-}$ and the molar ratio of the alkali metal to the dianion is at least about 2:1.

A still further aspect of the present invention is a method for making $H_4Ru_4(CO)_{12}$ in high yields. This method comprises establishing a reaction mixture comprising a slurry or a solvent containing the tetraanion $[Ru_4(CO)_{12}]^{4-}$ and a protic acid. The reaction mixture most conveniently can be the product reaction mixture resulting from the tetraanion synthesis as discussed above. The protic acid is added in a substantial stoichiometric excess relative to the tetraanion contained in the solvent. Reaction conditions include a temperature not exceeding about room temperature. Yields of the $H_4Ru_4(CO)_{12}$ can range as high as about 85% or higher based on the $Ru_3(CO)_{12}$ feed utilized for making the tetraanion used in this method. Again, this reaction may be effected either with or without isolation of a $[Ru_4(CO)_{12}]^{4-}$ salt.

A yet further aspect of the present invention is the expected high yield synthesis of $[H_3Ru_4(CO)_{12}]^{1-}$, $[H_2Ru_4(CO)_{12}]^{2-}$, and the new cluster $[HRu_4(CO)_{12}]^{3-}$ by controlled protonation of $[Ru_4(CO)_{12}]^{4-}$ as described above.

The invention also provides a method for making $[Ru_3(CO)_{11}]^{2-}$ by controlled reduction of $Ru_3(CO)_{12}$ using a carrier and a solvent similar to those used in the preparation of $[Ru_4(CO)_{13}]^{2-}$ but substituting an alkaline earth metal for the alkali metal used to prepare $[Ru_4(CO)_{13}]^{2-}$. The corresponding osmium anion $[Os_3(CO)_{11}]^{2-}$ may similarly be prepared by controlled reduction of $Os_3(CO)_{12}$ but in this case either an alkali metal or an alkaline earth metal may be used in the reaction mixture.

DETAILED DESCRIPTION OF THE INVENTION

The essence of the present invention is the disclosed controlled reduction procedure wherein from $Ru_3(CO)_{12}$ the dianion and tetraanion tetraruthenium carbonylates can be synthesized in high yield. Thereupon, controlled protonation leads to substantially quantitative yields of $[HRu_4(CO)_{13}]^{1-}$, $H_2Ru_4(CO)_{13}$, $[HRu_4(CO)_{12}]^{3-}$, $[H_2Ru_4(CO)_{12}]^{2-}$, $H_3Ru_4(CO)_{12}]^{1-}$ and $H_4Ru_4(CO)_{12}$. In addition to the high yields obtained, the syntheses disclosed herein are simple which makes commercial practice of the present invention attractive. A beneficial corollary of the high yields obtained by the present invention is that the desired cluster compounds can be easily and efficiently separated from the product reaction mixtures so that the high yields obtained by the process are practical high yields.

Referring to the controlled reduction of triruthenium dodecacarbonyl, $Ru_3(CO)_{12}$, such synthesis scheme operates by providing a source of electrons which are solvated by the solvent used in the process wherein an electron carrier transfers the electrons from the electron source to the substrate $Ru_3(CO)_{12}$ for its reduction. Accordingly, a suitable source of the electrons is an alkali metal which preferably is potassium, though can be lithium, sodium, rubidium, or cesium. Solvents which solubilize the electrons from the alkali metals preferably are ethers such as, for example, methylene chloride, tetrahydrofuran, dimethyl ether, diethyl ether, glymes, hexamethyl phosphoramide, and the like. Additional suitable solvents include liquid ammonia and alkyl amines. Of course, any solvent which will solvate the alkali metal electrons and is unreactive with the reactants and products of the process, i.e. non-participating in the reaction, suitably can find use in the present invention.

Suitable electron carriers for use in making $[Ru_4(CO)_{13}]^{2-}$, often referred to as dianion herein, include benzophenone, napthalene, anthracene, liquid ammonia, trimethylamine, crown ethers, cryptates, and the like. The common feature of these electron carriers which permits their use in the controlled reduction process of the present invention is that they associate with the electron source, eg. K, and remove electrons from the electron source. That is, suitable electron carriers have more of an affinity for the electron from the alkali metal, but less of an affinity for the electron than the $Ru_3(CO)_{12}$ substrate. Those skilled in this art will readily appreciate the proper choice of electron carriers suitable for use in the present invention and the factors which must be taken into account in making such choice.

In forming the reaction mixture, the molar ratio of the alkali metal to the substrate $Ru_3(CO)_{12}$ optimally is about 1.5:1, though this ratio can range up to as high as almost 3:1. Reaction conditions include establishing the reaction mixture in the substantial absence of water and molecular oxygen, and a reaction temperature not exceeding about room temperature, i.e. 25° C. Reduced yields are experienced if the reaction temperature exceeds about room temperature. The reaction time is not significant and generally sufficient reaction time is allowed for generation of about 70% or more of the theoretical amount of carbon monoxide by-product generated by the reaction.

The dianion can be recovered from the reaction mixture as a salt by addition of a solvent in which the salt is insoluble, eg. $CH_2Cl_2$ for $K_2[Ru_4(CO)_{13}]$. Alternatively, metathesis of the product reduction mixture leads to a variety of different salts of the dianion made by the process. Suitable salts for the metathesis reaction include amine salts such as $[(Ph_3P)_2N]Cl$, where Ph is a phenyl group, tetraalkyl quaternary ammonium salts, tetraphenyl quaternary ammonium salts, tetraalkyl phosphonium salts, tetraphenyl phosphonium salts, and mixed alkyl/aryl quaternary ammonium and phosphonium salts. Yields from the metathesis salt product can be as high as 70% or greater.

Characterization of the dianion include the following. Infrared spectra of $[Ru_4(CO)_{13}]^{2-}$ salts indicate the presence of bridging carbonyl groups with absorptions in the range of 1718–1815 $cm^{-1}$. The simpler infrared spectrum displayed by $[Ph_3P)_2N]_2[Ru_4(CO)_{13}]$ as compared with the corresponding sodium and potassium salts presumably is due to the lack of ion-pairing in this salt, as suggested by the studies of $[H_2Ru_4(CO)_{12}]^{2-}$ salts by Inkrott and Shore, *Inorg. Chem.*, 18, 2817 (1979). The $^{13}C$ NMR spectrum of $[(Ph_3P)_2N]_2[Ru_4(CO)_{13}]$, 35% enriched with $^{13}CO$, consists of a single peak at 223.7 ppm in $CD_2Cl_2/CHClF_2$ (1:2, v:v) down to −100° C. At −130° C., the lowest temperature attained, this peak disappears into the baseline.

For making $[HRu_4(CO)_{13}]^{1-}$, (the monoanion or anion as often referred to herein) the dianion suitably is protonated. The dianion substrate can be the dianion contained in the product reduction mixture disclosed above, or any salt of the dianion suitably can be disposed in a solvent which will dissolve the dianion salt. Accordingly, solvents for this protonation reaction preferably are those solvents used in the process for the controlled reduction of $Ru_3(CO)_{12}$ for production of the dianion as disclosed above. However, if the protonation is carried out using a phosphonum salt, it is desirable to use a chlorohydrocarbon such as methylene chloride as the solvent. Suitable protic acids include HCl, HBr, $H_2SO_4$, $H_3PO_4$ and even water for present purposes. While oxidizing acids may be used, for maximizing yields of the anion product oxidizing acids are excluded in the process. The proportion of protic or proton-donating acid should be adjusted to provide a molar ratio thereof to the dianion substrate of at least about stoichiometric and often a slight excess of protic acid is used on up to a molar ratio of about 2:1 of the protic acid to the dianion substrate. The exclusion of oxygen is preferred for maximizing yield of the anion product. Reaction temperatures should not exceed about room temperature in order to suppress degradation by-product formation in the process and reaction temperature as low as about 0° to −110° C., for example, provide very high yields of product. The anion product can be recovered from the reaction mixture in salt form by addition of a solvent to the product reaction mixture in which solvent the salt is insoluble. The anion salt is an apparently especially stable solid, though preliminary indications are that there may be slight stability problems of the anion in solution. Suitable salts of the anion include use of the cations as disclosed above for the metathesis reaction of the dianion product. Essentially quantitative yields of the anion salt can be expected from this reaction.

$[HRu_4(CO)_{13}]^{1-}$ may also be prepared by reacting $H_2Ru_4(CO)_{13}$ and $Ru_4(CO)_{13}^{2-}$ in a solvent. Preferably the reaction should be conducted at a temperature not exceeding about 0° C. and preferred solvents for the reaction are ethers, especially tetrahydrofuran.

In characterizing the anion salts, potassium and $(Ph_3P)_2N$ salts of $[HRu_4(CO)_{13}]^{1-}$ exhibited similar infrared spectra with weak bridging carbonyl absorptions at 1850 and 1830 cm$^{-1}$, respectively. The PMR spectrum of $[(Ph_3P)_2N][HRu_4(CO)_{13}]$ displayed a single, temperature independent hydride resonance at 25.84 down to $-80°$ C. in $CD_2Cl_2$. The $^{13}C$ NMR spectrum (35% enrichment) at $-58°$ C. consisted of a single sharp peak at 203.7 ppm in $CD_2Cl_2/CHClF_2$. At $-138°$ C., this peak broadened, another broad peak occured at 235 ppm, and peaks in the terminal carbonyl region appeared. Some of the terminal carbonyls are strongly coupled to hydrogen as evidenced by proton decoupling experiments.

For synthesis of $H_2Ru_4(CO)_{13}$ in high yield, the anion or dianion product reaction mixtures as described above suitably can be protonated with a protic acid. Alternatively, any salt of the anion or dianion dispersed in a solvent which dissolves said salts in solution also can be used as a feedstock in this protonation reaction. Accordingly, those solvents described above in the dianion process find utility in this synthesis scheme. Suitable acids include sulfuric acid, hydrochloric acid, hydrobromic acid, phosphoric acid, and the like. Very strong acids in large excess quantities are preferred for this reaction as the pK$_a$ of $H_2Ru_4(CO)_{13}$ has been determined to be 14.7 by Walker et al, JACS, 101, pp. 7428-7429 (1979). While water apparently does not interfere with this protonation reaction, its exclusion is desired for insuring maximization of yields of product. The temperature of the reaction is controlled so that no overheating with attendant decomposition is experienced. Thus, the reaction preferably is conducted at room temperature or less and preferably at about 0° C. Essentially quantitative yields of the $H_2Ru_4(CO)_{13}$ product are experienced by this reaction. Solvent extraction and chromatographic separation are the preferred methods for separation of the $H_2Ru_4(CO)_{13}$ product.

The controlled reduction procedure for synthesis of $[Ru_4(CO)_{12}]^{4-}$ can utilize substrates including $Ru_3(CO)_{12}$ and $[Ru_4(CO)_{13}]^{2-}$ or a salt thereof. Reaction conditions established for this synthesis broadly are the same as those conditions established for the controlled reduction of $Ru_3(CO)_{12}$ in making the dianion, except that the reaction temperature can range as high as about 80° C. though the temperature is preferably kept down to not more than 50° C. With either substrate, excess electrons are established in the reaction mixture in this process. For $Ru_3(CO)_{12}$ substrate this translates into a molar ratio of alkali metal to substrate of about 3:1 or greater. Note that with molar ratios of alkali metal to $Ru_3(CO)_{12}$ substrate between about 1½:1 and 3:1, likely a mixture of the dianion and tetraanion results. Note further that it has not been determined whether in this reaction the dianion is a necessary intermediate. For using the dianion or salt thereof substrate, the molar ratio of electron source or alkali metal to the substrate preferably is stoichiometric though higher ratios can be used at the expense of excess alkali metal reactant. It should be understood further that in some of the desired solvents, e.g., THF, the resulting tetraanion product is found in its insoluble salt form. Monitoring of carbon monoxide by-product gas again is a convenient method for following the completeness of the reaction. Yields of the tetraanion, or salt thereof, can range as high as about 90% or more based on the $Ru_3(CO)_{12}$ substrate. The infrared spectrum of $K_4Ru_4(CO)_{12}$ as a nujol mull exhibits very broad absorptions at 1978(m), 1938(m), 1865(s), 1845(s), 1790(s), and 1610(w) cm$^{-1}$. Insolubility of this compound in the solvents utilized thus far has precluded further spectral identification. It should be noted that the alkali metal salts may precipitate in the form of a cryptate or crown ether complex.

The parent cluster $H_4Ru_4(CO)_{12}$ can be produced from the tetraanion by a protonation procedure substantially as described above for synthesis of $H_2Ru_4(CO)_{13}$. Excess strong acids also are preferred for this protonation reaction as the pK$_a$ of $H_4Ru_4(CO)_{12}$ has been determined to be 11.7 by Walker et al, supra. Yields of $H_4Ru_4(CO)_{12}$ are quantitative which translates to about 85% yield based on the $Ru_3(CO)_{12}$ substrate which is converted to the tetraanion. By controlling the molar proportion of protic acid to the tetraanion, this protonation reaction also can be used for synthesizing $[HRu_4(CO)_{12}]^{3-}$, $[H_2Ru_4(CO)_{12}]^{2-}$ and $[H_3Ru_4(CO)_{12}]^{1-}$. To prepare each of these three intermediates, the protic acid should be added to the $[Ru_4(CO)_{12}]^{4-}$ anion in substantially the stoichiometric proportion i.e., one, two or three moles of acidic hydrogen respectively per mole of the tetraanion, that is to say per four moles of ruthenium. As mentioned above, the protonation reactions may be effected either with or without isolation of the salt of the tetraanion. Synthesis of the tetraanion followed by protonation may be a more economical method for commercial synthesis of the known clusters $[H_3Ru_4(CO)_{12}]^{1-}$ and $[H_2Ru_4(CO)_{12}]^{2-}$. The $[HRu_4(CO)_{12}]^{3-}$ compound is new.

$H_2Ru_4(CO)_{13}$ previously has been reported to exhibit catalytic activity in various isomerization reactions. The anion, dianion, and tetraanion synthesized herein are expected to exhibit catalytic activity or be instrumental in preparing neutral clusters therefrom which exhibit catalytic activity. Prior catalytic activity of transition metal carbonyl clusters is reported by Basset and Smith, Abstracts of Invited Talks, XIX International Conference on Pure and Applied Chemistry, Prague, Czechoslovakia, pp 161-164, (1978). Additionally, the clusters synthesized herein may find use as heterogeneous catalysts by suitable reaction with an acidic support analagous to such preparations as proposed by McVicker and Vannice, Exxon Research and Engineering Company, Corporate Pioneering Research Laboratories, Linden, New Jersey (1979). Further, the clusters synthesized herein may provide unusual catalytic activity by their decomposition onto a support to generate unique crystals of metallic ruthenium. Other valuable uses of the clusters synthesized herein likely will be discovered based on the successful synthesis of such clusters as reported herein. An excellent discussion in cluster catalysis also can be found in J. M. Basset and R. Ugo, Chapter 2, "Structure and Electronic Relations Between Molecular Clusters and Small Particles: An Essay to the Understanding of Very Dispersed Metals", Aspects of Homogeneous Catalysis, Vol. 3, D. Reidel, Dordrecht, Holland (1977). More particularly, the cluster complexes disclosed herein are useable as hydroformylation catalysts.

The anion $[Ru_3(CO)_{11}]^{2-}$ represents an intermediate stage of reduction between the starting material $Ru_3(CO)_{12}$ and the aforementioned dianion and tetraanion. There is spectroscopic evidence that the reduction of triruthenium dodecacarbonyl to the aforementioned dianion and trianion actually proceeds via $[Ru_3(CO)_{11}]^{2-}$ as a transient intermediate which cannot be isolated and which reacts with the starting material to give the tetraruthenium anions. If, however, a reaction mixture is established using a solvent and electron carrier of the type used to prepare the tetraruthenium dianion and tetraanion, but using as an electron source an alkaline earth metal rather than an alkali metal, the alkaline earth metal salt of $[Ru_3(CO)_{11}]^{2-}$ is relatively insoluble, so that further reduction is avoided. The preferred alkaline earth metal for use in this reaction is calcium, and during the reaction the temperature preferably does not exceed about room temperature. If desired, the calcium salt thus produced may be converted to other salts, such as amine salts, quaternary ammonium salts, phosphonium salts and arsonium salts by simple metathesis. Preferably the alkaline earth metal and the triruthenium dodecacarbonyl are present in the reaction mixture in about equimolar amounts.

The corresponding osmium dianion $[Os_3(CO)_{11}]^{2-}$ can be prepared in a similar manner from $Os_3(CO)_{12}$, but in this case either an alkaline metal or an alkaline earth metal may be used as the source of electrons for the reduction, since both the alkali metal and the alkaline earth metal salts of the osmium dianion are sufficiently insoluble to prevent further reduction of the dianion. The preferred alkali metal for use in this reduction is potassium, while the preferred alkaline earth metal is calcium. The preferred reaction conditions are exactly the same as those used for the preparation of the corresponding ruthenium dianion, and the alkali or alkaline earth metal is preferably present in the reaction mixture in about the stoichiometric amount, that is to say two moles of alkali metal or one mole of alkaline earth metal per mole of triruthenium dodecacarbonyl.

The following examples show how the present invention can be practiced but should not be construed as limiting. In this application, all units are in the metric system unless otherwise expressly indicated. Also, all citations referred to herein are expressly incorporated herein by reference.

EXAMPLES

EXAMPLE 1

Preparation of $K_2[Ru_4(CO)_{13}]$

Potassium metal (2.39 mmoles), benzophenone (2.35 mmoles), and triruthenium-dodecacarbonyl (1.45 mmoles) were placed in a reaction vessel held under a dry nitrogen atmosphere. The vessel was evacuated and about 10 ml of dry tetrahydrofuran (THF) was condensed therein. The vessel was thermostated and stirred at −78° C. for about 12 hours, warmed to room temperature, and stirred for another 24 hours. About 2.6 mmoles of CO (about 80% of theoretical) was evolved from the vessel during the reaction. The reaction proceeds according to the following equation.

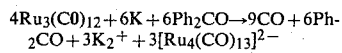

$K_2[Ru_4(CO)_{13}]$ was precipitated from solution by reducing the volume of THF to about 2 ml and adding $CH_2Cl_2$ until precipitation occurred. The yield of $K_2[Ru_4(CO)_{13}]$ was about 80% based on the starting $Ru_3(CO)_{12}$.

EXAMPLE 2

Preparation of $[(Ph_3P)_2N]_2[Ru_4(CO)_{13}]$

From a product reduction mixture prepared according to Example 1, the volume of THF solvent was reduced to about 5 ml. Approximately 3 ml of $CH_2Cl_2$ was condensed into the vessel at −78° C. Next, 2.35 mmoles of $[(Ph_3P)_2N]Cl$ was added to the vessel at −78° C. with stirring of the vessel's contents and the solution in the vessel warmed to room temperature. After 1 hour at room temperature, the solvent mixture was removed from the vessel and additional $CH_2Cl_2$ was condensed into the vessel at −78° C. The solution then was filtered at room temperature to give a free-flowing, white frit residue (KCl) and a deep red filtrate. Addition of diethyl ether to the filtrate resulted in reprecipitation of the desired product in about 70% yield.

EXAMPLE 3

Preparation of $K[HRu_4(CO)_{13}]$ $K_2[Ru_4(CO)_{13}]$ (0.10 mmoles) was placed in a reaction vessel held under a nitrogen atmosphere. The vessel was evacuated and 2 ml of THF was condensed into the vessel at −78° C. Anhydrous HCl gas was measured volumetrically (0.10 mmoles) and condensed into the vessel at −196° C. The vessel was warmed to −78° C. The reaction proceeds according to the following equation.

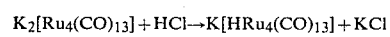

The solution was filtered at −78° C. to remove byproduct KCl. Addition of $CH_2Cl_2$ induced precipitation of the desired product.

EXAMPLE 4

Preparation of $H_2Ru_4(CO)_{13}$

To a vessel containing a product reduction mixture like that of Example 1 was attached an addition tube containing about 5 ml of concentrated $H_2SO_4$ and 5 ml of THF. The vessel was evacuated and cooled to 0° C. The acid mixture was allowed to drip into the vessel with vigorous stirring. The solution changed color from red to brown to red again. As soon as the solution was observed to return to a red color, the acid addition was terminated.

The vessel was opened to the atmosphere and its contents poured into a hexane/water mixture. Extraction with hexane was continued until the extracts were clear. The hexane extracts (about 2 liters) were dried over $MgSO_4$ and chromatographed on silica gel to yield 75% $H_2Ru_4(CO)_{13}$ based on the starting $Ru_3(CO)_{12}$.

EXAMPLE 5

Preparation of $K_4[Ru_4(CO)_{12}]$ from $Ru_3(CO)_{12}$

Potassium metal (3.06 mmoles), benzophenone (3.06 mmoles), and triruthenium dodecacarbonyl (1.02 mmoles) were placed in a reaction vessel held under a dry nitrogen blanket. The vessel was evacuated and about 15 ml of dry THF was condensed therein. The vessel was thermostated and stirred at 50° C. for 36 hours or until 100% of the theoretical amount of by-product CO was evolved from the vessel according to the following equation.

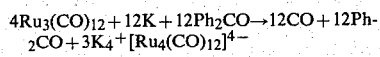
$$4Ru_3(CO)_{12} + 12K + 12Ph_2CO \rightarrow 12CO + 12Ph_2CO + 3K_4^+[Ru_4(CO)_{12}]^{4-}$$

The desired $K_4Ru_4(CO)_{12}$ was isolated by filtering the product reduction mixture and washing the filtered solid with THF. The yield of $K_4Ru_4(CO)_{12}$ was about 85–90% based on the $Ru_3(CO)_{12}$ feed.

EXAMPLE 6

Preparation of $K_4[Ru_4(CO)_{12}]$ from $K_2[Ru_4(CO)_{13}]$ $K_2[Ru_4(CO)_{13}]$ (0.12 mmoles), benzophenone (0.26 mmoles), and potassium metal (0.26 mmoles) were placed in a reaction vessel held under a dry nitrogen atmosphere. The vessel was evacuated and about 2 ml of THF was condensed therein. The vessel was thermostated and stirred at 50° C. until the reduction mixture was colorless and an orange-gold precipitate was formed. Approximately 100% of the theoretical amount of CO as evolved during the reaction according to the following equation.

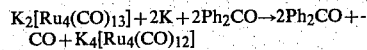
$$K_2[Ru_4(CO)_{13}] + 2K + 2Ph_2CO \rightarrow 2Ph_2CO + CO + K_4[Ru_4(CO)_{12}]$$

The desired $K_4[Ru_4(CO)_{12}]$ was isolated from the product reduction mixture by filtration and the filtered solid washed with THF. The yield of $K_4[Ru_4(CO)_{12}]$ was about 95% based on the dianion salt feed.

EXAMPLE 7

Preparation of $Ca[Ru_3(CO)_{11}]$ from $Ru_3(CO)_{12}$.

A glyme solution containing 1 mmole of calcium metal and 2 mmoles of benzophenone was added to triruthenium dodecacarbonyl held in a reaction vessel held under a dry nitrogen atmosphere. The vessel was evacuated and about 10 ml. of dry glyme were condensed therein. The reaction was allowed to proceed for 15 minutes at ambient temperature, after which time 80% of the theoretical amount of carbon monoxide had evolved. The reaction proceeds according to the following equation:

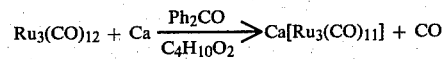
$$Ru_3(CO)_{12} + Ca \xrightarrow[C_4H_{10}O_2]{Ph_2CO} Ca[Ru_3(CO)_{11}] + CO$$

At the end of the 15 minute reaction period, the reaction mixture was immediately filtered and washed to give $Ca[Ru_3(CO)_{11}] \cdot 2C_4H_{10}O_2$ in 71% yield. Elemental analysis yielded the following results:

$Ca[Ru_3(CO)_{11}]$ Calc. Ca, 4.82; Ru, 36.46; C, 27.44; H, 2.42. Found Ca, 4.78; Ru, 34.14; C, 28.10; H 3.07.

The calcium salt product had the form of an orange powder which was very air and water sensitive. Its infrared spectrum taken in a Nujol mull showed a strong bridging carbonyl absorption at 1565 cm$^{-1}$ and an absorption at 1065 cm$^{-1}$ attributable to the coordinated glyme. Comparison of this infrared spectrum with that of the potassium salt of the corresponding osmium anion (discussed below) suggested that the anion has the three ruthenium atoms arranged at the vertices of an isosceles triangle, with the ruthenium at the unique vertex of the triangle having four CO groups coordinated therewith, each of the other rutheniums having three CO groups coordinated only therewith, while the eleventh CO group bridges both the rutheniums at the base of the isosceles triangle.

$Ca[Os_3(CO)_{11}]$ can be prepared in exactly the same manner starting from $Os_3(CO)_{12}$.

EXAMPLE 8

Preparation of $K_2[Os_3(CO)_{11}]$ from $Os_3(CO)_{12}$.

Potassium metal (2 mmoles), benzophenone (1 mmole) and triosmium dodecacarbonyl (1 mmole) were placed in a reaction vessel held under a dry nitrogen atmosphere. The vessel was evacuated and about 10 ml. of dry THF were condensed therein. The mixture was stirred for 3 hours at room temperature after which time 100% of the theoretical amount of carbon monoxide had been evolved and the solution had turned yellow-orange. The potassium salt was precipitated from the solution with a mixture of dimethyl ether and methylene chloride and washed with methylene chloride to give $K_2[Os_3(CO)_{11}]$ as a bright yellow-orange powder in 79% yield. Elemental analysis yielded the following results:

$K_2[Os_3(CO)_{11}]$ Calc. K, 8.17; Os, 59.62; C, 13.80. Found: K, 8.62; Os, 59.27; C, 13.60.

Dissolution of the salt in THF and addition of tetraphenylarsonium chloride yielded the corresponding tetraphenylarsonium salt $[Ph_4As]_2[Os_3(Co)_{11}]$.

The infrared spectrum of the potassium salt in THF displays a bridging carbonyl absorption at 1625 cm$^{-1}$, which is unchanged upon metathesis to the arsonium salt. This suggests a structure containing a single carbonyl bridge (as described above for the corresponding triruthenium dodecacarbonyl dianion), and this is confirmed by the low temperature $^{13}C$ nuclear magnetic resonance spectra, which were recorded in a 2:1, v/v dimethyl ether/THF mixture on a sample prepared from 25% $^{13}$C-enriched $Os_3(CO)_{12}$. At $-138°$ C., although a spectrum in the slow exchange limit has still not been attained, the spectrum shows (apart from two-temperature invariant peaks at 193 and 198 ppm. probably due to impurities), three peaks at 282.1, 202.8 and 186.1 ppm., having relative areas of 1:2:8 respectively. Even at $-130°$ C., the peak at 186.1 ppm is still broad and displays evidence of a shoulder on its upper side, suggesting that this peak is composite and would split at lower temperatures. Upon warming, the 282.1 peak disappears and at $-100°$ C. the peak at 186 ppm, is sharp indicating an exchange process equilibriating about half the carbonyls. At higher temperatures, coalescence of all the peaks occurs to give a single resonance at 196.7 ppm, in good agreement with the weighted average of 197.8 ppm.

We claim:

1. A ruthenium carbonylate anion of the formula $[H_xRu_4(CO)_{13}]^{(2-x)-}$ where x is 0 or 1.

2. A salt of a ruthenium carbonylate anion of the formula $[H_xRu_4(CO)_{13}]^{(2-x)-}$ where x is 0 or 1, wherein the cation is an alkali metal, a cation derived from an amine, a quaternary ammonium cation or a phosphonium cation.

3. A salt according to claim 2 wherein said cation is an alkali metal.

4. A salt according to claim 3 wherein said alkali metal is potassium, namely $K_2[Ru_4(CO)_{13}]$ or $K[HRu_4(CO)_{13}]$.

5. A salt according to claim 2 wherein said cation is $[(Ph_3P)_2N]^+$ namely $[(Ph_3P)_2N]_2[Ru_4(CO)_{13}]$ or

[(Ph₃P)₂N][HRu₄(CO)₁₃], where Ph represents a phenyl group.

6. A method for making a ruthenium carbonylate complex of the formula $[H_yRu_4(CO)_{13}]^{(2-y)-}$ where y is 0 or 1 by the controlled reduction of $Ru_3(CO)_{12}$ which comprises: establishing a reaction mixture held under substantially anhydrous conditions and oxygen-depleted conditions at a temperature not above about room temperature of said $Ru_3(CO)_{12}$; an alkali metal; a carrier compound which will carry an electron produced by the ionization of said alkali metal of said $Ru_3(CO)_{12}$; and a solvent which will at least solubilize the electron-bearing form of said carrier compounds, the molar ratio of said alkali metal to said $Ru_3(CO)_{12}$ being restricted to be at least about 1.5:1 but less than 3:1.

7. A method according to claim 6 wherein said alkali metal is K, Li, Na, Rb, or Cs.

8. A method according to claim 7 wherein said alkali metal is K.

9. A method according to claim 6 wherein said carrier compound is benzophenone, hexamethylphosphoramide, naphthalene, anthracene, liquid ammonia, a cryptate, or a crown ether.

10. A method according to claim 8 or 9 wherein said carrier is benzophenone.

11. A method according to claim 6 wherein said solvent is an ether, liquid ammonia, or an alkylamine.

12. A method according to claim 11 wherein said solvent is tetrahydrofuran, dimethyl ether, diethyl ether, a glyme, or liquid ammonia.

13. A method according to claim 10 wherein said solvent is tetrahydrofuran.

14. A method according to claim 6 wherein said molar ratio is between about 1.5 and 2.0.

15. A method according to claim 6 wherein said reaction mixture is maintained substantially free from protic acids and the ruthenium carbonylate complex produced is the anion $[Ru_4(CO)_{13}]^{2-}$.

16. A method according to claim 15 wherein an alkali metal salt of said $[Ru_4(CO)_{13}]^{2-}$ is separated from said reaction mixture.

17. A method according to claim 16 wherein said separated salt is $K_2[Ru_4(CO)_{13}]$.

18. A method according to claim 15 wherein said reaction mixture is subjected to metathesis with a salt selected from an amine salt, a quaternary ammonium salt, or a phosphonium salt; and the resulting $[Ru_4(CO)_{13}]^{2-}$ salt is recovered.

19. A method according to claim 18 wherein said salt is a tetraalkyl or tetraaryl phosphonium salt, a tetraalkyl or tetraaryl quaternary ammonium salt, an alkylamine salt, or an arylamine salt.

20. A method according to claim 6 wherein to said reaction mixture is added a protic acid, including water, in a molar proportion of about 1:1 to 2:1 relative to said $[Ru_4(CO)_{13}]^{2-}$ in said reaction mixture, under conditions substantially free of molecular oxygen at a temperature not above about room temperature and the ruthenium carbonylate complex produced is $[HRu_4(CO)_{13}]^{1-}$.

21. The method of claim 20 wherein said protic acid is HCl or HBr.

22. The method of claim 20 wherein said temperature is between about −110° and 0° C.

23. A method according to claim 6 wherein to the reaction mixture is added a substantial stoichiometric excess of protic acid, the temperature of said reaction mixture being maintained at about room temperature or less during said protic acid addition, and the ruthenium carbonylate complex produced is $H_2Ru_4(CO)_{13}$.

24. A method according to claim 23 wherein said acid is HCl, $H_2SO_4$, or HBr.

25. The method of claim 23 wherein said temperature is maintained between about −100° and 0°.

26. The method of claim 25 wherein said temperature is maintained at about −78° C.

27. A method of making $[HRu_4(CO)_{13}]^{1-}$ or $H_2Ru_4(CO)_{13}$ which comprises establishing a reaction mixture comprising a solvent containing the dianion $[Ru_4(CO)_{13}]^{2-}$ dissolved therein and a protic acid under conditions substantially free of molecular oxygen at a temperature not substantially above about room temperature.

28. A method according to claim 27 wherein said protic acid is HCl HBr, $H_2SO_4$ or $H_3PO_4$.

29. A method according to claim 27 wherein said solvent is an ether, a chlorohydrocarbon liquid ammonia or a trialkylamine.

30. A method according to claim 29 wherein said solvent is tetrahydrofuran, dimethyl ether, diethyl ether, methylene chloride or a glyme.

31. A method according to claim 27 wherein said temperature is between about −110° and +25° C.

32. A method according to claim 27 wherein the molar ratio, between said protic acid and said $[Ru_4(CO)_{13}]^{2-}$ is between about 1:1 and 2:1 and the product is $[HRu_4(CO)_{13}]$.

33. A method according to claim 32 wherein said protic acid is water.

34. A method according to claim 32 wherein said $[HRu_4(CO)_{13}]^{1-}$ is recovered from said reaction mixture as an alkali metal salt, an amine salt, a quaternary ammonium salt or a phosphonium salt.

35. A method according to 34 wherein said cation of said salt is an alkali metal.

36. A method according to claim 35 wherein said salt is $K[HRu_4(CO)_{13}]$.

37. A method according to claim 34 wherein said salt is $[(Ph_3P)_2N][HRu_4(CO)_{13}]$ wherein Ph is a phenyl group.

38. A method of making $[HRu_4(CO)_{13}]^{1-}$ which comprises reacting $H_2Ru_4(CO)_{13}$ with $[Ru_4(CO)_{13}]^{2-}$ in a solvent.

39. A method according to claim 38 wherein said reaction is conducted at a temperature not exceeding about 0° C.

40. A method according to claim 38 wherein said solvent is an ether.

41. A method according to claim 40 wherein said solvent is tetrahydrofuran.

42. A method of making $H_2Ru_4(CO)_{13}$ which comprises establishing a reaction mixture comprising a solvent containing the anion $[HRu_4(CO)_{13}]^{1-}$ dissolved therein and a protic acid under conditions substantially free of molecular oxygen at a temperature not substantially above about room temperature.

43. A method according to claim 42 wherein said protic acid is HCl, HBr, $H_2SO_4$ or $H_3PO_4$.

44. A method according to claim 42 wherein said solvent is an ether, a chlorohydrocarbon, liquid ammonia or a trialkylamine.

45. A method according to claim 44 wherein said solvent is tetrahydrofuran, dimethyl ether, diethyl ether, methylene chloride or a glyme.

46. A method according to claim 42 wherein said temperature is between about −110° and +25° C.

47. A ruthenium carbonylate anion of the formula $[H_qRu_4(CO)_{12}]^{(4-q)-}$ where q is 0 or 1.

48. A salt of a ruthenium carbonylate anion of the formula $[H_qRu_4(CO)_{12}]^{(4-q)-}$ where q is 0 or 1, wherein the cation is an alkali metal, a cation derived from an amine, a quaternary ammonium cation or a phosphonium cation.

49. A salt according to claim 48 where said cation is an alkali metal.

50. A salt according to claim 49 wherein said alkali metal is potassium, namely $K_4[Ru_4(CO)_{12}]$ or $K_3[HRu_4(CO)_{12}]$.

51. A method of making a ruthenium carbonyl complex of the general formula $[H_rRu_4(CO)_{12}]^{(4-r)-}$ where r is 0, 1, 2, 3, or 4 which comprises establishing a reaction mixture held under substantially anhydrous and oxygen depleted conditions at a temperature not above about 80° C., said reaction mixture comprising a ruthenium carbonyl starting material selected from the group consisting of $Ru_3(CO)_{12}$ and $[Ru_4(CO)_{13}]^{2-}$, an alkali metal, a carrier compound which will carry an electron produced by the ionization of said alkali metal to said starting material, and a solvent which will solubilize at least the electron-carrying form of said carrier compound.

52. A method according to claim 51 wherein said temperature is not above about 50° C.

53. A method according to claim 51 wherein said alkali metal is K.

54. A method according to claim 51 wherein said carrier compound is benzophenone, hexamethylphosphoramide, naphthalene, anthracene, liquid ammonia, a cryptate or a crown ether.

55. A method according to claim 53 or 54 wherein said carrier is benzophenone.

56. A method according to claim 51 wherein said solvent is an ether, liquid ammonia, or an alkylamine.

57. A method according to claim 56 wherein said solvent is tetrahydrofuran, dimethyl ether, diethyl ether, a glyme, or liquid ammonia.

58. A method according to claim 57 wherein said solvent is tetrahydrofuran.

59. A method according to claim 51 wherein said starting material is $Ru_3(CO)_{12}$ and the molar ratio of said alkali metal to said $Ru_3(CO)_{12}$ is at least about 1.5:1.

60. A method according to claim 59 wherein said molar ratio is at least about 3:1.

61. A method according to claim 51 wherein said starting material is $[Ru_4(CO)_{13}]^{2-}$ and the molar ratio of said alkali metal to said $[Ru_4(CO)_{13}]^{2-}$ is at least about 2:1.

62. A method according to claim 61 wherein said molar ratio is between about 2:1 and 3:1.

63. A method according to claim 51 wherein said reaction mixture is maintained substantially free of protic acid and $[Ru_4(CO)_{12}]^{4-}$ is produced.

64. A method according to claim 63 wherein a salt of said $[Ru_4(CO)_{12}]^{4-}$ is separated from said reaction mixture, the cation of said salt being an alkali metal free or in the form of a cryptate or crown ether complex, a cation derived from an amine, a quaternary ammonium cation or a phosphonium cation.

65. A method according to claim 64 wherein said separated salt is $K_4[Ru_4(CO)_{12}]$.

66. A method according to claim 51 wherein a protic acid is added to the reaction mixture in a molar proportion of about one mole of acidic hydrogen per four moles of ruthenium, the temperature being maintained not substantially above about room temperature during the addition of said protic acid, thereby producing $[HRu_4(CO)_{12}]^{3-}$.

67. A method according to claim 66 wherein said temperature is between about −110° and 0° C.

68. A method according to claim 51 wherein a protic acid is added to the reaction mixture in a molar proportion of about two moles of acidic hydrogen per four moles of ruthenium, the temperature being maintained not substantially above room temperature during the addition of said protic acid, thereby producing $[H_2Ru_4(CO)_{12}]^{2-}$.

69. A method according to claim 68 where said temperature is between about −110° and 0° C.

70. A method according to claim 51 wherein a protic acid is added to the reaction mixture in a molar proportion of about three moles of acidic hydrogen per four moles of ruthenium, the temperature being maintained not substantially above room temperature during the addition of said protic acid, thereby producing $[H_2Ru_4(CO)_{12}]^{1-}$.

71. A method according to claim 70 wherein said temperature is between about −110° and 0° C.

72. A method according to claim 51 wherein a substantial stoichiometric excess relative to ruthenium of a protic acid is added to said reaction mixture, the temperature being maintained not substantially above room temperature during the addition of said protic acid, thereby producing $H_4Ru_4(CO)_{12}$.

73. A method according to claim 72 wherein said protic acid is HCl, $H_2SO_4$, $H_3PO_4$ or HBr.

74. A method according to claim 72 wherein said temperature is between about −110° and 0° C.

75. A method of making a ruthenium carbonyl complex of the general formula $[H_sRu_4(CO)_{12}]^{(4-s)-}$ where s is 1, 2, 3, or 4 which comprises establishing a reaction mixture comprising a slurry or a solvent containing the tetraanion $[Ru_4(CO)_{12}]^{4-}$ dissolved therein and a protic acid at a temperature not substantially above about room temperature.

76. A method according to claim 75 wherein said temperature is between about −110° and 0°.

77. A method according to claim 75 wherein said protic acid is HCl, $H_2SO_4$, $H_3PO_4$ or HBr.

78. A method according to claim 75 wherein said protic acid is present in said reaction mixture in a molar proportion of about one mole of acidic hydrogen per four moles of ruthenium, thereby producing $[HRu_4(CO)_{12}]^{3-}$.

79. A method according to claim 75 wherein said protic acid is present in said reaction mixture in a molar proportion of about two moles of acidic hydrogen per four moles of ruthenium, thereby producing $[H_2Ru_4(CO)_{12}]^{2-}$.

80. A method according to claim 75 wherein said protic acid is present in said reaction mixture in a molar proportion of about three moles of acidic hydrogen per four moles of ruthenium, thereby producing $[H_3Ru_4(CO)_{12}]^{1-}$.

81. A method according to claim 75 wherein said protic acid is present is said reaction mixture in a stoichiometric excess relative to said ruthenium thereby producing $H_4Ru_4(CO)_{12}$.

82. A method of making a ruthenium carbonyl complex of the general formula $[H_tRu_4(CO)_{12}]^{(4-t)-}$ where t is 2, 3 or 4 which comprises establishing a reaction mixture comprising a solvent containing the trianion $[HRu_4(CO)_{12}]^{3-}$ dissolved therein and a protic acid at a temperature not substantially above about room temperature.

83. A method according to claim 82 wherein said temperature is between about −110° and 0° C.

84. A method according to claim 82 wherein said protic acid is HCl, H$_2$SO$_4$, H$_3$PO$_4$ or HBr.

85. A method according to claim 82 wherein said protic acid is present in said reaction mixture in a molar proportion of about one mole of acidic hydrogen per four moles of ruthenium, thereby producing [H$_2$Ru$_4$(CO)$_{12}$]$^{2-}$.

86. A method according to claim 82 wherein said protic acid is present in said reaction mixture in a molar proportion of about two moles of acidic hydrogen per four moles of ruthenium, thereby producing [H$_3$Ru$_4$(CO)$_{12}$]$^{1-}$.

87. A method according to claim 82 wherein said protic acid is present in said reaction mixture in a stoichiometric excess relative to said ruthenium, thereby producing H$_4$Ru$_4$(CO)$_{12}$.

88. A Group VIII carbonylate anion of the general formula [M$_3$(CO)$_{11}$]$^{2-}$ where M is Ru or Os.

89. A salt of a Group VIII carbonylate anion of the general formula [M$_3$(CO)$_{11}$]$^{2-}$ where M is Ru or Os, wherein the cation is an alkali metal, an alkaline earth metal, a cation derived from an amine, a quaternary ammonium cation, a phosphonium cation or an arsonium cation.

90. A salt according to claim 89 wherein M is Ru and said cation is an alkaline earth metal cation.

91. The salt according to claim 90 wherein said cation is calcium, namely Ca[Ru$_3$(CO)$_{11}$].

92. The salt according to claim 91 in the form of crystals containing about two moles of glyme of crystallization, namely Ca[Ru$_{3;L}$(CO)$_{11}$]·2C$_4$H$_{10}$O$_2$.

93. A salt according to claim 89 wherein M is Os and said cation is an alkali metal cation, an alkaline earth metal cation or an arsonium cation.

94. A salt according to claim 93 where said cation is potassium, calcium or [Ph$_4$As]$^+$ where Ph represents a phenyl group, namely K$_2$[Ru$_3$(CO)$_{11}$], Ca[Ru$_3$(CO)$_{11}$] and [Ph$_4$As]$_2$[Ru$_3$(CO)$_{11}$].

95. A method of making [Ru$_3$(CO)$_{11}$]$^{2-}$ by the controlled reduction of Ru$_3$(CO)$_{12}$ which comprises: establishing a reaction mixture of said Ru$_3$(CO)$_{12}$; an alkaline earth metal; a carrier compound which will carry an electron produced by the ionization of said alkaline earth metal to said Ru$_3$(CO)$_{12}$; and a solvent which will at least solubilize the electron-bearing form of said carrier compound, thereby producing Ca[Ru$_3$(CO)$_{11}$].

96. A method according to claim 95 wherein said alkaline earth metal is Ca.

97. A method according to claim 95 wherein said carrier is benzophenone, hexamethylphosphoranide, naphthalene, anthracene, liquid ammonia, a cryptate or a crown ether.

98. A method according to claim 97 wherein said carrier is benzophenone.

99. A method according to claim 95 wherein said solvent is an ether, liquid ammonia, or an alkylamine.

100. A method according to claim 99 wherein said solvent is tetrahydrofuran, dimethyl ether, diethyl ether, a glyme, or liquid ammonia.

101. A method according to claim 100 wherein said solvent is a glyme.

102. A method according to claim 95 wherein said alkaline earth metal and said Ru$_3$(CO)$_{12}$ are present in said reaction mixture in about equimolar amounts.

103. A method according to claim 95 wherein said reaction mixture is established at a temperature not above about room temperature.

104. A method according to claim 95 wherein said Ca[Ru$_3$(CO)$_{11}$] is subjected to metathesis with a salt selected from an amine salt, a quaternary ammonium salt, a phosphonium salt or an arsonium salt and the resulting [Ru$_3$(CO)$_{11}$]$^{2-}$ salt is recovered.

105. A method according to claim 104 wherein said salt is a tetraalkyl or tetraaryl phosphonium salt, a tetraalkyl or tetraaryl quaternary ammonium salt, an alkyl amine salt, an arylamine a tetraalkyl or tetraalkyl arsonium salt or a tetraphenyl arsonium salt.

106. A method of making [Os$_3$(CO)$_{11}$]$^{2-}$ by the controlled reduction of Os$_3$(CO)$_{12}$ which comprises: establishing a reaction mixture of said Os$_3$(CO)$_{12}$; an alkali or alkaline earth metal; a carrier compound which will carry an electron produced by the ionization of said metal to said Os$_3$(CO)$_{12}$; and a solvent which will at least solubilize the electron-bearing form of said carrier compound, thereby producing an alkali or alkaline earth metal salt of said [Os$_3$(CO)$_{11}$]$^{2-}$.

107. A method according to claim 106 where said metal is K or Ca.

108. A method of according to claim 106 wherein said carrier compound is benzophenone, hexamethylphosphoramide, naphthalene, anthracene, liquid ammonia, a cryptate, or a crown ether.

109. A method according to claim 108 where said carrier is benzophenone.

110. A method according to claim 106 wherein said solvent is an ether, liquid ammonia, or an alkylamine.

111. A method according to claim 110 wherein said solvent is tetrahydrofuran, dimethyl ether, diethyl ether, a glyme, or liquid ammonia.

112. A method according to claim 111 wherein said solvent is tetrahydrofuran.

113. A method according to claim 106 wherein said metal and said Os$_3$(CO)$_{12}$ are present in said reaction mixture in about stoichiometric amounts.

114. A method according to claim 106 wherein said reaction mixture is established at a temperature not above about room temperature.

115. A method according to claim 106 wherein said salt of [Os$_3$(CO)$_{11}$]$^{2-}$ is subjected to metathesis with a salt selected from an amine salt, a quaternary ammonium salt, a phosphonium salt or an arsonium salt; and the resulting [Os$_3$(CO)$_{11}$]$^{2-}$ is recovered.

116. A method according to claim 115 wherein said salt is a tetralkyl or tetraaryl quaternary ammonium salt, an alkylamine salt, an arylamine salt or a tetraalkyl or tetraaryl asonium salt.

117. A method according to claim 116 wherein said salt is a tetraphenylarsonium salt.

118. A method according to claim 117 where said salt is tetraphenylarsonium chloride.

* * * * *